(12) United States Patent
Duncan (10) Patent No.: US 8,961,387 B2
(45) Date of Patent: Feb. 24, 2015

(54) TRANSCUTANEOUS MAGNETIC ENERGY TRANSFER DEVICE

(75) Inventor: Coley B. Duncan, Webster, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/502,301

(22) PCT Filed: Oct. 14, 2010

(86) PCT No.: PCT/US2010/052682
§ 371 (c)(1),
(2), (4) Date: Jul. 6, 2012

(87) PCT Pub. No.: WO2011/047160
PCT Pub. Date: Apr. 21, 2011

(65) Prior Publication Data
US 2012/0277520 A1    Nov. 1, 2012

Related U.S. Application Data

(60) Provisional application No. 61/252,436, filed on Oct. 16, 2009.

(51) Int. Cl.
*A61M 1/12* (2006.01)
*A61N 1/378* (2006.01)
*A61M 1/10* (2006.01)

(52) U.S. Cl.
CPC ........... *A61N 1/3787* (2013.01); *A61M 1/1036* (2014.02); *A61M 1/10* (2013.01); *A61M 1/127* (2013.01); *A61M 2205/3515* (2013.01)
USPC .................................. 600/16; 600/17; 607/61

(58) Field of Classification Search
USPC ...................... 600/16, 17; 607/2, 61
See application file for complete search history.

(56) References Cited

U.S. PATENT DOCUMENTS

| | | | |
|---|---|---|---|
| 5,693,091 A * | 12/1997 | Larson et al. | 623/3.27 |
| 5,741,316 A | 4/1998 | Chen et al. | |
| 5,945,762 A * | 8/1999 | Chen et al. | 310/171 |
| 6,092,531 A * | 7/2000 | Chen et al. | 128/899 |
| 2001/0003802 A1* | 6/2001 | Vitale | 623/3.11 |
| 2002/0161274 A1 | 10/2002 | French et al. | |
| 2006/0093872 A1 | 5/2006 | Howard et al. | 429/9 |
| 2009/0204141 A1* | 8/2009 | Dlugos et al. | 606/191 |

* cited by examiner

*Primary Examiner* — Carl H Layno
*Assistant Examiner* — Pamela M Bays
(74) *Attorney, Agent, or Firm* — Patent Technologies, LLC; Robert S. Gunderman, Jr.

(57) ABSTRACT

Transcutaneous magnetic energy transfer to drive a VAD or other implanted medical device can be supplied through two spinning (or otherwise moving) permanent magnets, or a moving permanent magnet and a moving ferric material, or a moving permanent magnet and a coil or an array of coils, One part is implanted under the patient's skin, so that the skin does not have to be broken for a connection to take place.

14 Claims, 9 Drawing Sheets

TRANSCUTANEOUS MAGNETIC ENERGY TRANSFER DEVICE

REFERENCE TO RELATED APPLICATION

The present application claims benefit of U.S. Provisional Application No. 61/252,436, filed Oct. 16, 2009 and International Application No. PCT/US10/52682, filed Oct. 14, 2010, whose disclosures are hereby incorporated in their entirety into the present disclosure.

FIELD OF THE INVENTION

The present invention is directed to a device for transferring energy across a patient's skin and/or mucosa and more particularly to such a device which does so through the movement of a permanent magnet or magnets.

DESCRIPTION OF RELATED ART

An artificial heart is a man-made pump that entirely replaces the heart. A ventricular assist device (VAD) is a man-made pump that is installed to pump, usually in parallel with the heart with the heart being left in place.

A VAD requires a lot of energy, too much energy for a single battery to power it very long without recharging. Whereas a battery in a pacemaker may last between five and fifteen years, a VAD requires considerably more power, as it must pump 45-90 gallons per hour. Therefore, current battery technology is unlikely to power a VAD for more than 24 hours before requiring a recharge. A satisfactory means for supplying power to a VAD has not yet been devised. The original means for supplying power to an electric VAD is a battery that is worn on a belt pack. A cable passes through the skin to supply power to the VAD. That cable passing through the skin is the greatest weakness of that design. It creates a portal of entry for bacteria which leads directly to the heart. The rate of infection is officially 20-50% and unofficially thought to be much higher, thus severely limiting the acceptance of VAD's. By contrast, the rate of infection with a pacemaker, which is totally implantable, is 1-3%. A means of safely and reliably transferring the large amount of power required to supply a VAD across unbroken skin without significant heat generation is sorely needed.

Currently VAD's are approved for bridge to transplant. They are put into patients who are awaiting cardiac transplant with the intent to keep the patient alive until a heart transplant can be done. There are 100,000 people each year in the United States who develop end stage congestive heart failure and who could qualify for heart transplants, yet only about 2,000 heart transplants are done in the US each year. Within one year 70% of those 100,000 patients have died. One of the things keeping VAD's from being destination therapy (the ultimate solution to the patients' problem instead of just a bridge) is the lack of a good transcutaneous energy transfer system.

The majority of current VAD designs are continuous flow electric pumps. Some people refer to those as semi-pulsatile pumps because there is a regular, intermittent peak of flow that occurs with each heart contraction.

One solution known in the art is to implant a coil beneath the patient's skin. When a charging unit including another coil is placed near the implanted coil, the two coils act as a transformer to transfer power to the VAD. That is called a coil/coil energy transfer system (TETS). The electric sending coil on the outside of the skin has high frequency AC current flowing through it. That AC current creates a time varying magnetic field that induces a flow of electrons within a receiving coil implanted under the skin. Those coils must be aligned precisely in order for energy to transfer efficiently. That precise alignment is difficult to achieve. The high frequency of the current in the sending coil leads to significant heat generation. The problems with alignment and heat generation mean that the patient may need to remain attached to the external power source, with the resulting impact on quality of life. That high frequency current also poses a significant danger to the patient should a short circuit occur in the system. A means of safely and reliably transferring the large amount of power required to supply a VAD across unbroken skin without significant heat generation is sorely needed.

It is known in the art to actuate a switch in a pacemaker by use of a large permanent magnet outside of the patient's body. However, it is not known to transfer enough energy to operate a device by any such technique.

In an unrelated field of endeavor, a common device found in many chemistry laboratories is a magnetic stir bar stirrer. Those devices also often contain heaters, but the heater would not be useful for the purpose of the present invention and will therefore not be discussed further. That device is basically an electric motor that spins a horseshoe magnet or a metal bar with a magnet embedded in each end, one with the south pole up and the other with the north pole up. A separate magnetic bar is placed within the laboratory glassware containing a liquid to be stirred. When the glassware is placed on the stirrer, the magnetic stir bar will align itself with the magnet in the stirrer base. As the motor in the base is turned on, the stir bar will spin in synchrony with the magnet below it.

Some ventricular assist device designs use an electromagnetic bearing similar to the magnetic stir bar stirrer just described. The magnetic field generated by the stator both floats and spins the impellor. That creates a circumstance in which, while there are moving parts, there is no friction between the parts of the pump, but only of blood against the parts of the pump. However, the application of such a bearing to transfer energy across unbroken skin is as yet unknown in the art.

SUMMARY OF THE INVENTION

It will be understood from the above that a need exists in the art to provide for the transfer through unbroken skin of sufficient energy to power a VAD or similar device. It is therefore an object of the invention to provide a transcutaneous transfer of energy to operate a VAD or any other implanted device which combines minimal risk of infection, efficiency of energy transfer and little generation of heat.

It is another object of the invention, in at least some embodiments, to combine two apparently competing goals to ensure reliability, namely, redundancy and a minimum number of parts.

It is still another object of the invention, in at least some embodiments, to provide such a transfer of energy using a device having low weight, low bulk, ergonomic shape, low heat generation, low torque, safe, reliable/longevity, short charge times and long run times.

To achieve the above and other objects, in at least one embodiment of the invention, a system is provided for transcutaneous magnetic energy transfer, the system comprising: a first component implanted in a patient's body, the first component comprising a first movable object which is connected to a medical device in the patient's body to power the medical device; and a second component disposed outside of the patient's body, the second component comprising a second movable object for transferring mechanical energy to the first movable object by causing the first movable object to move; wherein one of the first and second movable objects is a permanent magnet, and wherein the other movable object is a permanent magnet or an object comprising a ferric material subject to be influenced by a magnetic field. As an illustrative example, the external power supply for the VAD can be connected to an electric motor that will spin a magnet. That spinning magnet will be placed over a magnet implanted under the skin. The second magnet will be attached to an electrical generator. That generator will be connected to the motor driving the VAD and/or charging a battery. That would represent a motor/generator set connected by the magnetic coupling achieved between the two magnets. Instead of spinning magnets, the magnets can oscillate or move in any other manner; however, rotating magnets are preferred. Also, either one of the magnets can be replaced by an object including a ferric material. Any number of magnets or components of ferric metal could be used in any embodiment of the invention.

Low weight, low bulk, ergonomic shape and low torque are aimed at making the device practical for smaller people and at providing comfort. Short charge times and long run times would increase the quality of life for the recipients. Reliability is important because failure could have disastrous effects. The longevity of the system is important because each time part or all of the system is replaced, the patient must go through a surgery, and surgeries carry risk. The patients who would receive such a device would by definition have congestive heart failure. They would tend to be older and would likely have other serious underlying diseases. That would place those patients at increased risk for any surgery. To replace some of the components would be relatively minor surgery, but to replace the VAD would be major surgery. Each time the chest is entered by a surgeon, there is scarring and fibrosis making the next surgery much more difficult. It would be better for those patients to retain their hardware as long as possible without needing replacement.

There are two difficulties to be overcome in implementing that design. The first is keeping the two magnets (or other components) involved in the transcutaneous magnetic energy transfer aligned with one another.

One way to overcome that is to use magnets to connect the two devices involved in energy transfer. Another would be to anchor the receiving unit that is to be under the skin to strong tissues such as bone so that it did not move. That could also help to keep the receiving unit from being spun by the torque being applied to it by the sending unit. The farther the anchors could be placed from the center of the rotational axis of the generator, the more leverage that could be provided to counteract the torque.

Another way to overcome the problem of torque is to increase the speed, since power is proportional to speed times torque. The disadvantage of that solution is the speed (rpm's) can lead to increased heat and increased wear on the device. That is a particularly a concern for the implanted components that are more difficult to cool and to replace. A third solution would be counter-rotation. Multiple receiving units could be mounted in a single unit. They could be placed and the direction of their spin could be such that they would counteract each other's torque. Ideally, such a system would have two motor-generator sets with two permanent magnetic couplings spinning of the same axis, but with different diameters of the circle in which their magnets spin so that the magnetic fields would not interfere. Those motor generator sets would spin in opposite directions to counter each other's torque, much like the counter-rotating blades on a helicopter or counter-rotating propellers on an outboard motor. The sending unit could then be clipped to a device that was anchored to the skin using a glue such as that used to attach colostomy bags or some similar type of adhesive. The sending unit could have a handle (s) or other protrusion(s) protruding to one or more sides that could be held by a hand or by a retaining device to provide leverage to counteract the torque it would be produced by the spinning of the magnet and the energy being transferred through the magnetic lock.

The second problem would be that both the transfer device and the pump itself both use powerful magnets. The strength of the magnets and their positioning would need to be chosen such that unwelcome interference would not occur.

The sending and receiving units could be made of materials and designed in such ways as to move heat where it is desired and to resist moving it where it is not desired. The sending unit could have fins on the side away from the body to dissipate heat into the air by convection. The surface of the sending unit against the skin could be made of material to insulate it against transmitting its heat into the body or of heat conducting materials to draw away heat generated by the receiving unit. The sending and/or receiving unit could have an impellor with a magnet embedded within it attached to the main drive shaft or independent of the drive shaft but driven, directly or indirectly, by the magnet of the sending unit that could circulate cooling fluid within or from the sending and/or receiving unit to dissipate heat generated. The sending unit could have an active cooling system, such as, but not limited to, a fan, a refrigeration system, a thermo-electric or piezo-electric cooling device, a liquid cooling system with a radiator, ice or an endothermic reaction. The sending and/or the receiving unit could be sealed such that a vacuum could be pulled on the chamber containing the magnet and the motor or generator. Also, the chamber could be filled with an inert gas.

The rotational magnetic energy transferred into the body is described here as being converted into electrical energy using a generator. The VAD itself could be brought out to just underneath the skin so that the spinning of the magnet could directly turn the impellor in the pump, a direct drive pump. That would eliminate power loss and the production of heat that would occur when rotational magnetic mechanical energy is converted into electrical energy, transmitted internally to the pump and then converted back into mechanical energy.

The disadvantage of that arrangement would be that the blood would have to travel a longer distance away from and then back to the heart although blood does already travel a similar distance to and from VAD's implanted within the abdomen. That design might not work with electromagnetic bearing VAD's as it is also likely that the magnet on the sending unit would draw the impeller to that side of the pump, causing the impeller to create friction against the pump wall. It could easily be made to work with a VAD using a mechanical bearing design.

The best shape for a direct drive pump would be that of a disk rather than a cylinder. That allows for a larger diameter circle of spin for the magnets allowing for lower rpm's and higher torque. Also, a cylinder shaped pump has its long axis parallel to the skin while a disk shaped pump has its long axis perpendicular to the skin. Perpendicular is preferred for a direct drive pump because its long axis would line up with the long axis of the magnet being spun over the skin. A direct drive pump could have a motor/generator on the opposite side of the pump that could function as a generator to charge a battery while in direct drive mode and as a motor to drive the pump while the sending unit is disengaged. (That would be a single unit that could function as either a motor or a generator and would be different from the motor/generator set described in an embodiment of the present invention where there is a motor outside of the body and a generator inside of the body and those two are connected by a permanent magnet coupling.)

The motor/generator could have multiple coil sets along its long axis such that a single coil set could drive the pump and multiple coil sets could charge the battery. That would allow us to meet the objective of charge times being much shorter than the run times, giving the patient more freedom and higher quality of life. If the magnetic unit is still on the body but is not driving the VAD, it should be removed immediately so that the internal battery power is not used to spin the sending unit. The patient could remove it himself, but it would be helpful if the sending unit could move the external magnet away from the internal magnet by popping up or falling off of the receiving unit. If the sending unit magnet is not removed from proximity to the receiving unit magnet, the circuit on the motor could be opened so that motor in the sending unit did not become a generator to recharge an external battery, providing further drain on the internal battery.

That design should also incorporate an internal battery to provide continuous power when the magnetic connection is intentionally or unintentionally broken. If sufficient battery capacity is available, the patient could go extended periods of time without being connected to the sending unit. If a much more limited battery supply is available, an alarm should sound when the generator is not being spun, although some mechanism could be included to turn off the alarm when desired. That battery backup could allow for showering, etc., without the external battery pack.

The rotational magnetic energy within the body could be transferred internally to the pump using hydraulic fluid or a spinning cable such as is used to actuate a speedometer.

The present invention does not need to be limited only to VAD's or heart pumps, but could be used any time a power is needed to be transferred across intact skin. It could power any implanted medical device, currently existing or yet to be invented. It could drive the implanted medical device directly (or through any number of power transfer mechanisms) by spinning or otherwise moving a magnet, and/or it could be produce electricity to directly power the implanted medical device and/or charge a battery to be used to power the device.

Heart pumps and VAD's have been in use for many years with continuous and ongoing problems with infection, yet that solution has not previously been proposed.

In another embodiment, if a permanent magnet is required, or more desirable, the device could be simplified such that the spinning magnet outside of the body would spin over the coil inside of the body and directly induce electrical current. That device would have no moving parts inside of the body and would therefore have a much longer life expectancy. It is also possible that that arrangement might not require the same degree of accuracy of alignment of axes that the two permanent magnets would require. The inventor's investigations suggest that that is not as likely to be successful as the motor/generator set, but it is still a possibility.

Another, less desirable solution would be a coil outside of the body that spun a magnet inside of the body which in turn drove a generator. That would be simpler than motor/magnet/magnet/generator, but the simplicity would be gained outside of the body.

Magnetic energy can be transferred by movement of the magnetic field in other ways such as, but not limited to, oscillation. The core of the idea is the movement of a permanent magnet to send and/or receive energy across the skin to power an implanted medical device.

If the sending unit is being powered by external batteries, it could have at least two power supply connectors so the sending unit could remain connected to one battery while changing the other. The sending unit could drain power from only one battery at a time so it could completely drain one battery and switch to the other fully charged battery while the user changes the drained battery.

The sending and receiving units could be configured as broad flat disks, making the circle in which the magnets spin large. The motor and generator could be large diameter, very short cylinders. It may be possible for the magnets for the transfer of energy also to be the permanent magnets in the motor and generator. The disadvantage to that broad, flat design is that flat motors and generators are not, in general, as efficient as cylindrical units in which the axis of rotation is longer than the diameter. Therefore, it may be desirable to construct the motor and/or generator in a longer thinner cylindrical configuration.

The motor driving the sending device could have a regulator on it that would prevent the motor from accelerating beyond a certain speed if the receiving unit was not engaged in providing back pressure against the motor. It may be desirable to have the device be able to turn off the motor for the sending unit after a certain period of time if it senses that it is not driving the receiving unit.

The overall system could have any number of redundancies built into it. There could be two receiving units, two battery/control units and possibly two ventricular assist devices. The system could be designed in such a way that failure in a single component would not cause failure of one half or all of the system. As an example, it could be designed so that if one of the receiving units failed, both ventricular assist devices and both battery/control units could still be operational. Two ventricular assist devices could be installed either in tandem (in series) or in parallel. If installed in parallel, they could either share inflow and outflow tracts or could be tied into the ventricle and the aorta separately. Having two VAD's could result in requiring only half the output being delivered from each VAD resulting in reducing the size and weight of each individually and/or increasing the life expectancy of each VAD by running them at lower outputs. There could also be redundancy of the parts making up the various components of the system. An example would that the motor and the generator could have multiple sets of coils such that one set of coils could run the motor or produce power from the generator, respectively, should one or more coil sets fail. A battery/control unit could have more than one controller in a single unit. The controller and/or battery could have the ability to isolate a defective battery cell and still function on the remaining working cells.

The concern with parallel installation of VAD's is that blood flow would likely cease through the failed pump, possibly leading to clotting. That generally does not occur with a singular ventricular assist device because the heart often can push some blood through the failed pump. If there were a working pump in parallel, any blood flow pushed by the heart would likely go through the path of least resistance, which would be the working pump. If clotting occurred, it is possible that that clotting could propagate down the inflow and outflow tracts and possibly obstruct the flow of the working pump.

The advantage of the tandem installation would be that, if the failed pump would allow adequate passive flow through its impeller, the working pump could prevent clotting within the failed pump. If the failed pump would not allow adequate flow through its impeller, the failure of either pump would result in the inability of either pump to function. Also, if the pump that failed lost pieces of itself into the lumen that flowed downstream to the other pump, that could result in the failure of the downstream pump. Embolism of pieces during pump failure is something very much to be avoided by appropriate pump design inasmuch as that could result in cerebral vascular accident and other thromboembolic injuries.

In other words, two pumps are desirable only if the failure of one pump leaves the other pump still functioning. That would mean that, if one pump failed, the patient would have another pump that could function until the failed pump was replaced. However, if the failure of one pump resulted in the failure of the second, the risk of total pump failure would be doubled. In that scenario, having two pumps would not be in the patient's best interest.

The system could be compartmentalized. It could be designed in such a way that a single failed component could be removed without having to remove all or a large portion of the system. An example of lack of compartmentalization is the HeartMate II from Thoratec Corporation of Pleasanton, Calif., U.S.A. Its electric drive cable is hard wired into the VAD. If it is damaged, the cable itself must be repaired in place or the cable and pump must be replaced together. In particular, the ventricular assist device should not need to be removed for the failure of any other component. It would be particularly advantageous if the ventricular assist device could be separated from its tubing such that the tubing could be left sewn in and the ventricular assist device replaced. It would also be advantageous in a parallel installation of ventricular assist devices if the inflow and outflow tubing for one of the pumps could be clamped off without injury to the tubing such that the patient could effectively be on bypass with one pump running while the other pump was replaced. That would make the surgery for replacing ventricular assist devices a much less serious operation.

There may be other ways of isolating one pump from the circulatory system while leaving the other running, such as valves, although any complex mechanism left exposed to blood flow will create a propensity to generate blood clots. A little bit of complexity in the operating room would not be so great a concern as complex valves built into the system and remaining there throughout the life of the device waiting for the time when the patient might be taken to the operating room for pump replacement.

Regardless of how bypass is accomplished, it is likely that, if one ventricular assist device needs replacement, the other will be done at the same time, because the patient would already be in the operating room with both VAD's exposed and accessible, the failure of one pump would raise concerns that the other may fail soon and there are only so many times that the chest can be entered due to scarring and fibrosis.

The system could use AC or DC power. Also, while it is likely that power transfer and storage will be done with electricity, the invention could use any number of means to transfer power, including but not limited to, direct drive or energy transfer using hydraulics, flexible cables, belts, drive shafts, flywheels or gears.

A brushless motor could be used for the sending unit. It would be expected that currently available or yet to be developed motor and motor controller technology could be used to optimize the system.

Many patients with heart failure also have chronic obstructive pulmonary disease (COPD). Many patients with severe COPD require supplemental oxygen at home. The sending unit could be made to function safely in an oxygen-rich environment such that it would not create electrical sparks that might start a fire. Each system could have two sending units for each charge. They need to be constructed in such a way that they can be carried in carry-on luggage on an airplane inasmuch as the loss of those devices in lost luggage could result in the death of the patient. The sending units need to be rugged yet small and lightweight. The sending units could be made to operate on all international currents. It could come with adapter plugs for all international currents. It could be designed to sense the amount of current being supplied to it and adapt automatically much the way a modern laptop does. It could have built-in surge protection. It could be made to operate on 12-volt current from an automobile. It could also have available external batteries for when the patient will be in areas where electricity may not be available.

The internal components should be able to stand up to high-altitude (low pressure) and scuba diving pressures up to 10 atmospheres (330 feet). It is likely that it will be recommended to recipients of that device to not participate in potentially hazardous activities such as scuba diving. Many patients will not listen to nor abide by the advised restrictions. To take those patients into account, the present system should be implemented as a robust and sturdy device.

Yet another embodiment involves incorporating pacemaker and automatic implantable cardiac defibrillator (AICD) technology into the ventricular assist device system. That will allow the control modules and batteries to be available to perform those additional functions and will allow data collection and interventions to occur through a single (although perhaps redundant) central location. Data collection could include the measurement of any physiologic parameter that could be used to adjust the output of the device to match patient demand. That could include, but does not need to be limited to, pulse, respiratory rate, cardiac arrhythmias, and physical activity. Temperature could be monitored to detect device infection early. The system should be able to monitor itself and diagnose faults or impending failures including the heat of the components and the status of the internal battery or batteries. The internal components of the system could communicate with each other by wire or by internal telemetry such as transmission via electromagnetic spectrum. The system would be able to communicate with an outside control unit via telemetry via means, such as but not limited to, electromagnetic spectrum. That would allow for such things as transmission of data collected by the internal control unit and transmission of instructions and/or reprogramming from the external control unit to the internal control unit. The system could give audible alarms for any condition that could pose a danger to the patient, such as but not limited to, low battery power, need for maintenance or failures or impending failures.

The batteries have been disclosed as including the control modules, but it is possible that the control modules will be incorporated into the receiving units. It is also possible that a unit will have a receiving unit, control module and battery in a single unit, although that might concentrate too much bulk in a single location. The concentration of multiple functional units into a single unit should not impair the ability of those individual components to function should one of the components within that unit fail. There could be any number of separations or groupings of the individual components.

One major concern is eddy current, which is a swirl of electrons generated when a magnet is spun in front of a metal capable of conducting electricity. The sending and receiving units, especially their faces, ideally would be constructed of material that will not generate eddy current or will generate minimal eddy current. Ideally, the device should be constructed such that wires are unlikely to come between the sending and receiving units. However, there will need to be some slack in the wires to allow for movement. Eddy current within the skin itself will occur but should be at such very low levels that it should not be a problem at the low frequencies (rpm's) that that device will function.

The battery should preferably be a lithium titanate or similar battery. Lithium-ion batteries can be recharged only between 300 and 700 times and therefore can only be used in that application between six months and a year; they can also explode, especially if charged incorrectly. Lithium titanate batteries can be recharged many more times and still retain a much higher percentage of their original charge capacity and are much less likely to explode when charged incorrectly. In addition, they recharge rapidly and generate little heat when recharged.

Another battery that might be used is a $LiFePO_4$ battery. There is a version of that battery, recently developed at the Massachusetts Institute of Technology, which has the ability to be charged in seconds rather than minutes. Of course, any other suitable battery, now existing or later developed, could be used. The ideal characteristics for a battery for that application are a high charge capacity to weight ratio, high charge capacity to volume ratio, the ability to retain a high percentage of charge capacity after many recharges, the ability to be recharged quickly, low heat generation with charging and discharging, and low likelihood of exploding or leaking. If a battery were to be developed that was soft and/or flexible, those would also be desirable characteristics for a battery to store energy from that device.

Another problem with some batteries is memory, especially in nickel cadmium batteries. Whether memory really occurs in those batteries is debated, but it is clear that those batteries, and to a lesser extent nickel metal hydride batteries, have problems with crystal formation at the cathode plates and, to a lesser extent, their anode plates which results in reduced charge capacity. That problem with crystal formation is more likely to occur with disuse, overcharging and with failing to fully discharge a battery before recharging it. A battery that is able to be charged without fully discharging it would be a more desirable battery.

It is expected that embodiments of the invention would use any battery that meets a desirable mix of the above listed characteristics for storing within the body power generated by that magnetic transcutaneous energy transfer device. It is expected that the internal battery would have rounded, smooth edges and be shaped to fit within the space it is to occupy to make it more comfortable for the patient.

More than one battery might be placed within one patient to allow for redundancy and to spread out the size and weight of bulky hardware. The control unit of that system should be able to monitor the battery or batteries and charge and discharge them with the intent to increase battery life. In a system with multiple batteries, the controller could draw power from only one battery at a time allowing for a full discharge of each battery. The controller could draw most its power from one battery while doing a periodic slow discharge of another battery for the purpose of battery reconditioning. The controller could run the VAD directly off of the receiving unit while charging the battery or batteries at the same time. The controller could charge or discharge all of the internal batteries at once, separately one at a time or in any combination.

The problem with driving only one generator or being driven by only one motor is that there would be only one rotor in each sending unit and each receiving unit without a counterrotating rotor to counteract the spin. Such a unit could be constructed so that the torque of the rotor and the smaller bar spinning in the same direction would be equivalent to the torque of the larger bar spinning in the opposite direction, except that the torque is transferred to the housing from the stator and in turn from the rotor, likely resulting in little counter torque. The motors and/or generators would not have the bars holding the permanent magnets directly attached to their shafts, but could have intervening mechanisms of power transfer, including but not limited to gears, wheels, belts, pulleys, drive shafts, friction plates, hydraulics, and flexible drive cables. The axis of rotation of the bars need not be the same as or even parallel to the axis of rotation of the motor and/or generator, but could be offset and parallel or at any angle. The bars or disks could be replaced by any other shape that would balance on its spin axis.

The rotor and attached half of the permanent magnetic coupling of the implanted generator could float in an electromagnetic bearing to reduce, if not eliminate, friction with the intent to increase the life of the implanted generator. It seems possible that that could be done with the rotor and attached half of the permanent magnetic coupling of the motor of the sending unit, but the additional complexity and power consumption of that approach would probably not be worth it for something that can easily be replaced should it fail.

Embodiments of the invention could be shielded against EMP (electromagnetic pulses).

Wherever skin is referred to in the present application as the site for energy transfer, we assert that the description of the device or associated embodiments would also include mucosa or any barrier or gap. Any time the term magnet or magnets is used in the present disclosure, we mean a permanent magnet or permanent magnets, respectively. For the purpose of the present disclosure, anything said about a VAD could also apply to an artificial heart. Disclosures regarding energy transfer could apply to any implanted medical device that requires or could benefit from the recharging of a battery or requires or could benefit from transferring energy across the skin to directly power the implanted medical device.

BRIEF DESCRIPTION OF THE PREFERRED EMBODIMENTS

Preferred embodiments of the invention will be set forth in detail with reference to the drawings, in which.

DETAILED DESCRIPTION OF THE PREFERRED EMBODIMENTS

Preferred embodiments of the invention will now be set forth in detail with reference to the drawings, in which like reference numerals refer to like elements throughout.

Figure 1:
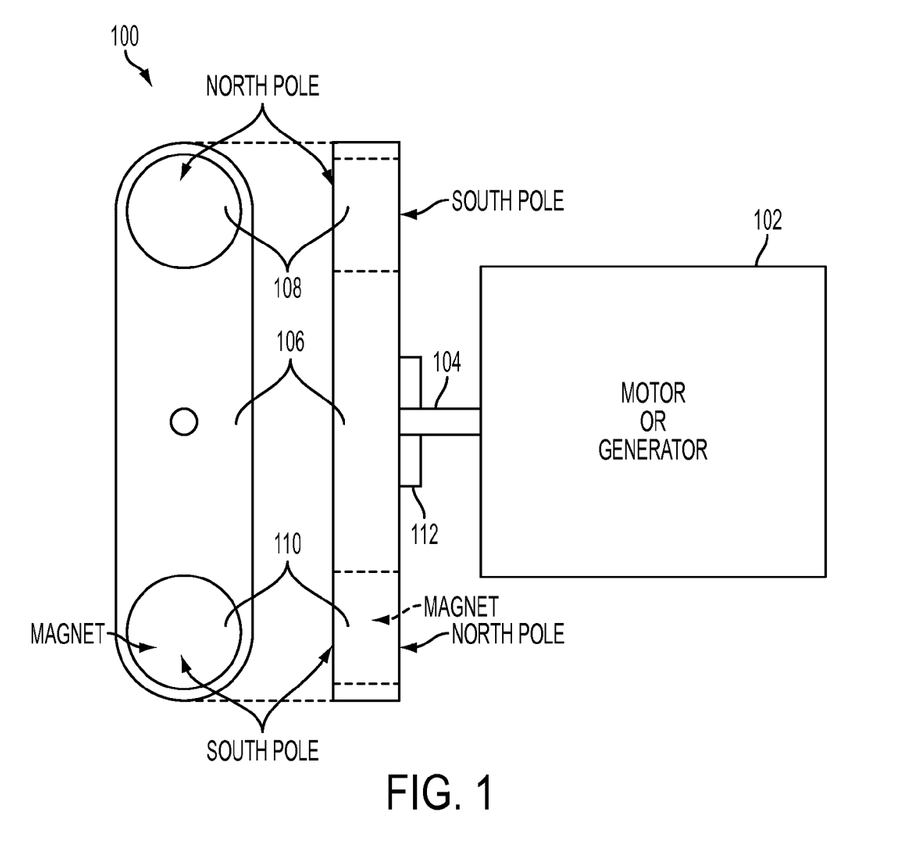
FIGS. 1 and 1A-1C show a motor or generator with one-half of a permanent magnetic coupling. Also shown is the face of the bar holding the permanent magnets of the permanent magnetic coupling.

FIG. 1 shows an assembly 100 including a motor or generator 102 attached via a shaft 104 to a bar or other rotor 106 forming one-half of a permanent magnetic coupling. Also shown is the face of the rotor 106 holding the permanent magnets 108, 110 of the permanent magnetic coupling. In the assembly 100, or in any other assembly disclosed herein as having at least one moving part, bearings 112 can be provided to float such a moving part.

Figure 1A:
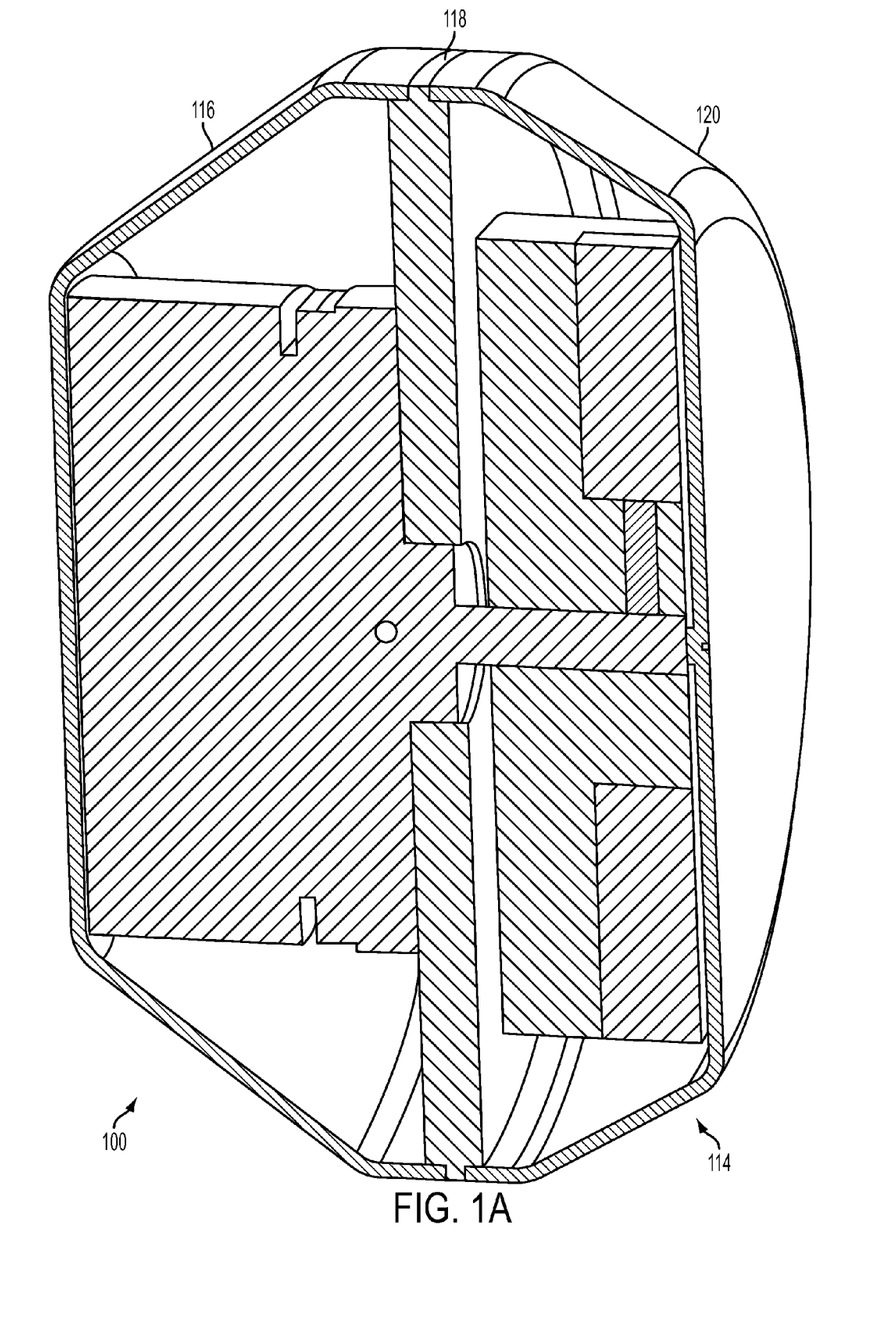
Figure 1B:
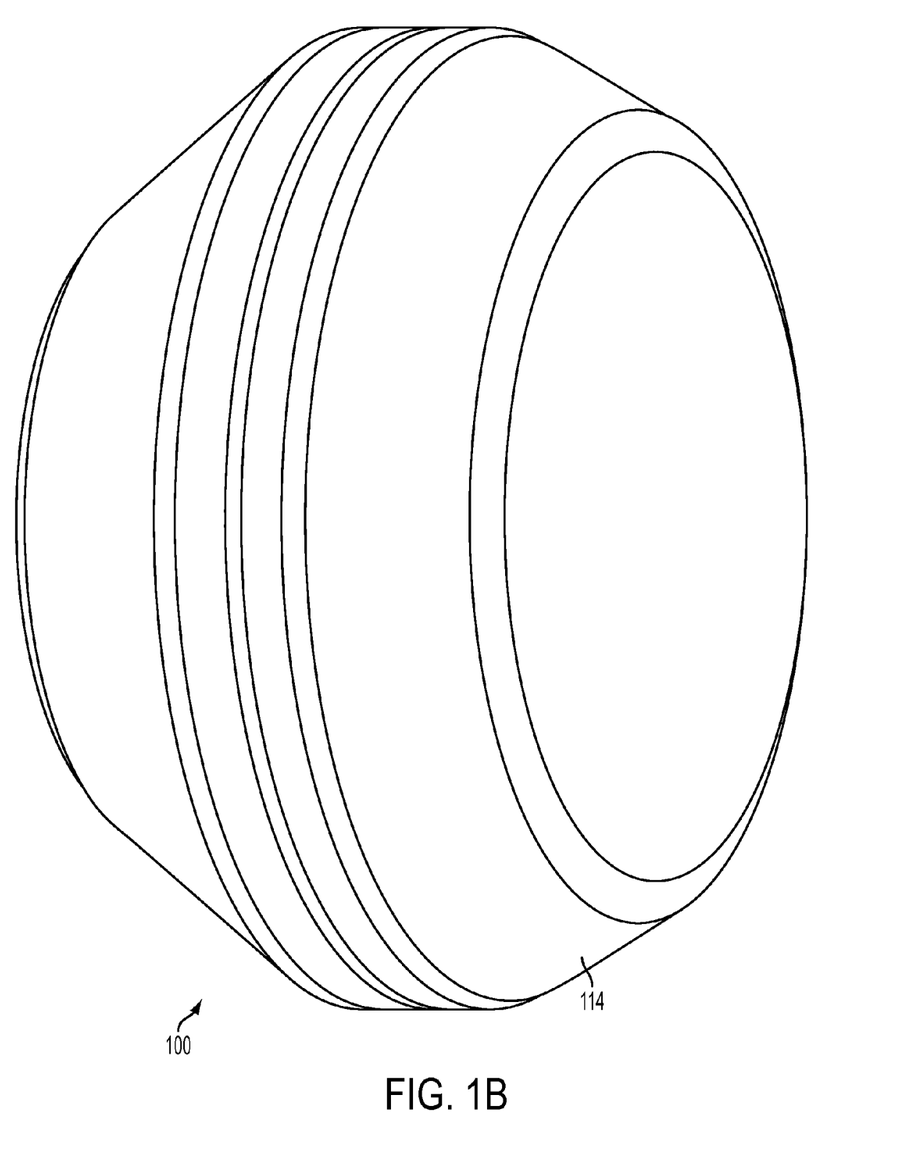
Figure 1C:
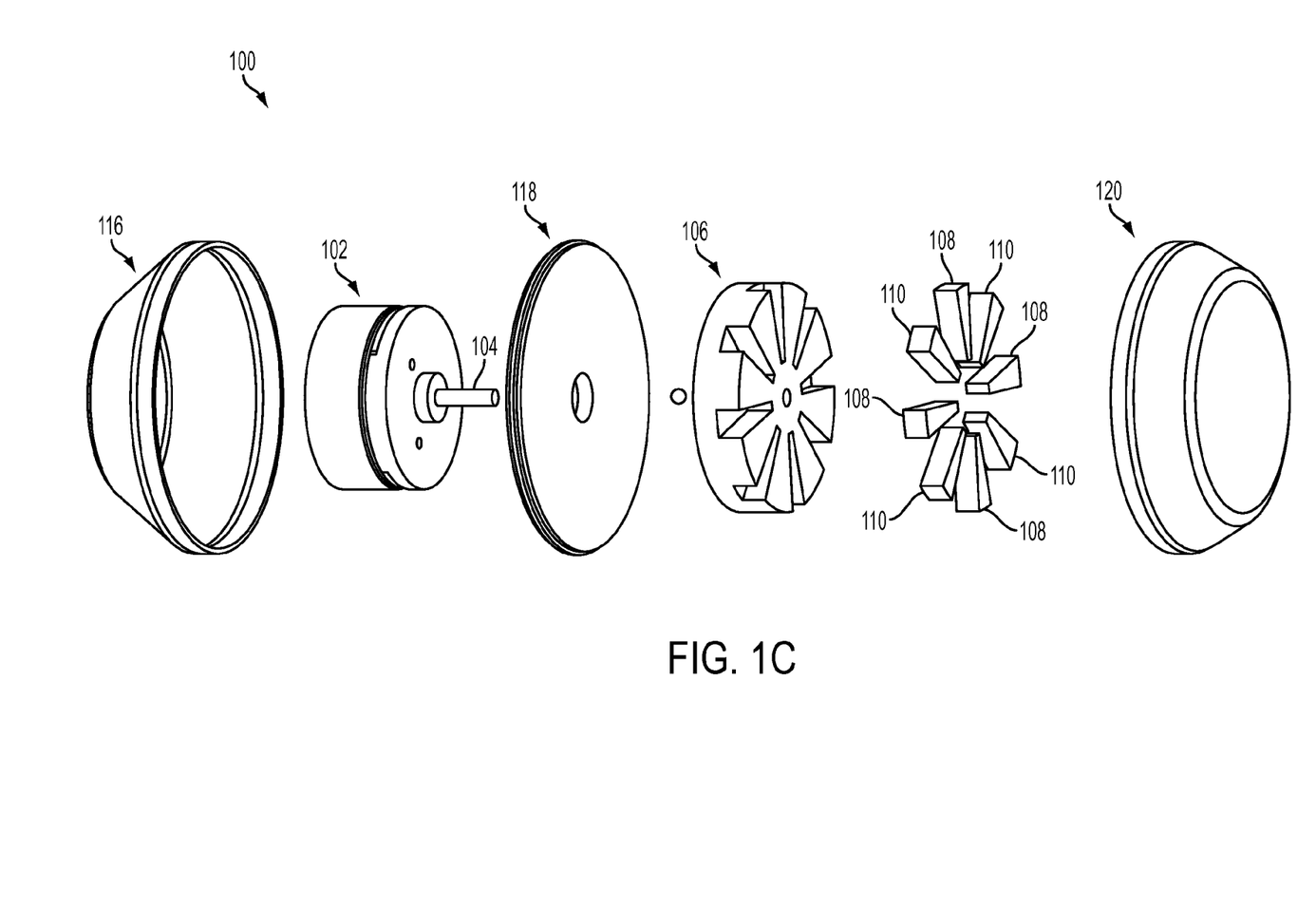

The assembly 100 is shown in greater detail in the sectional view of FIG. 1A, the external perspective view of FIG. 1B and the exploded view of FIG. 1C. The housing 114 includes housing components 116, 118 and 120.

Figure 2:
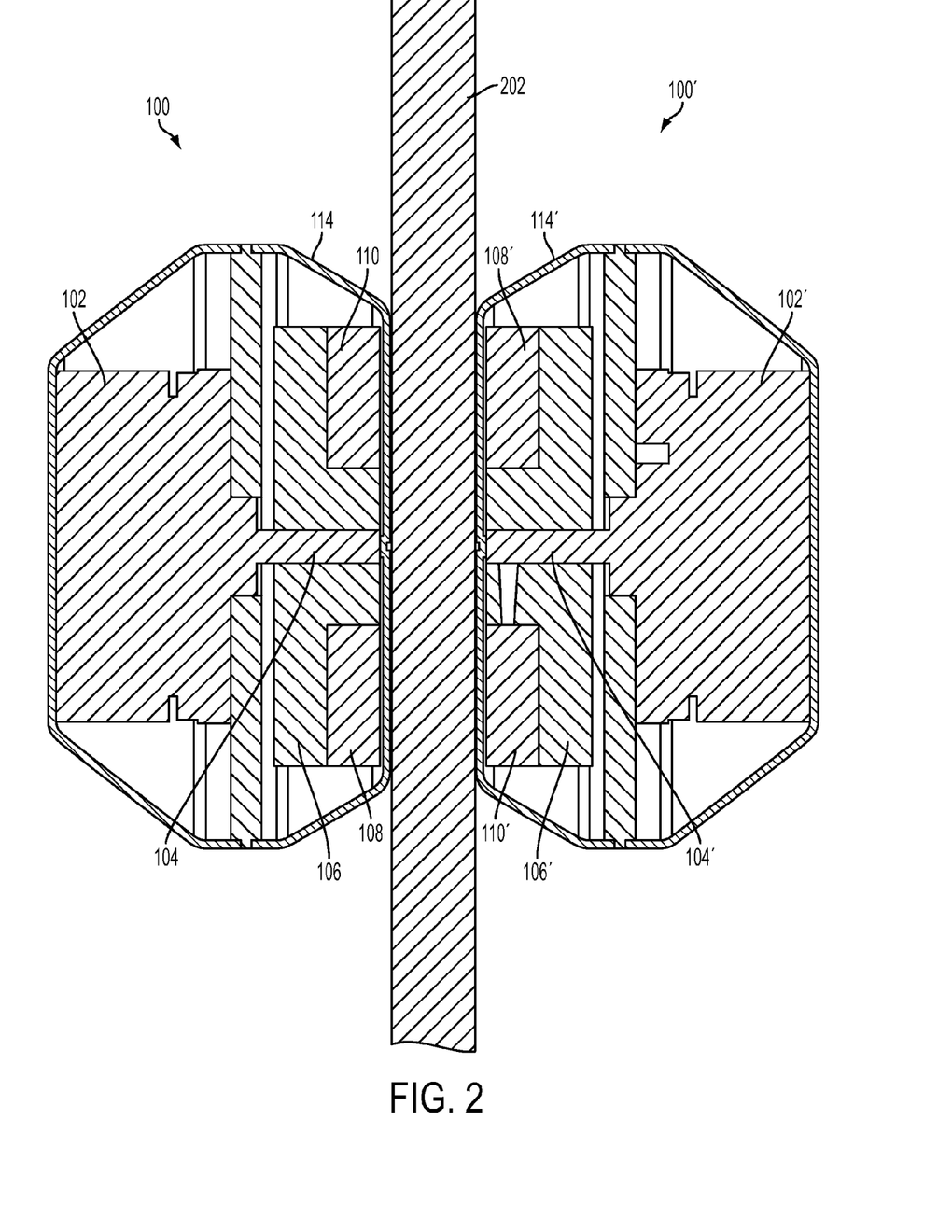
FIG. 2 shows the outside and inside of the body positioned across a barrier, e.g., skin or mucosa.

FIG. 2 shows a system 200 using the assembly 100 of FIG. 1 to transfer energy across a barrier 202 such as skin or mucosa. Outside of the body is an assembly 100 in a housing 114. In the present embodiment, in the assembly 100 outside of the body, the motor or generator 102 functions as a motor, so that the assembly 100 functions as a sending unit. Surgically implanted within the patient's body is another assembly 100' having a generator 102' and a shaft 104'. The rotor 106' and the magnets 108' and 110' are designed for magnetic coupling with the rotor 106 and the magnets 108 and 110 in the manner disclosed herein, so that the assembly 100' functions as a receiving unit. The housing 114' is designed for implantation in any of the manners disclosed herein.

Figure 3:
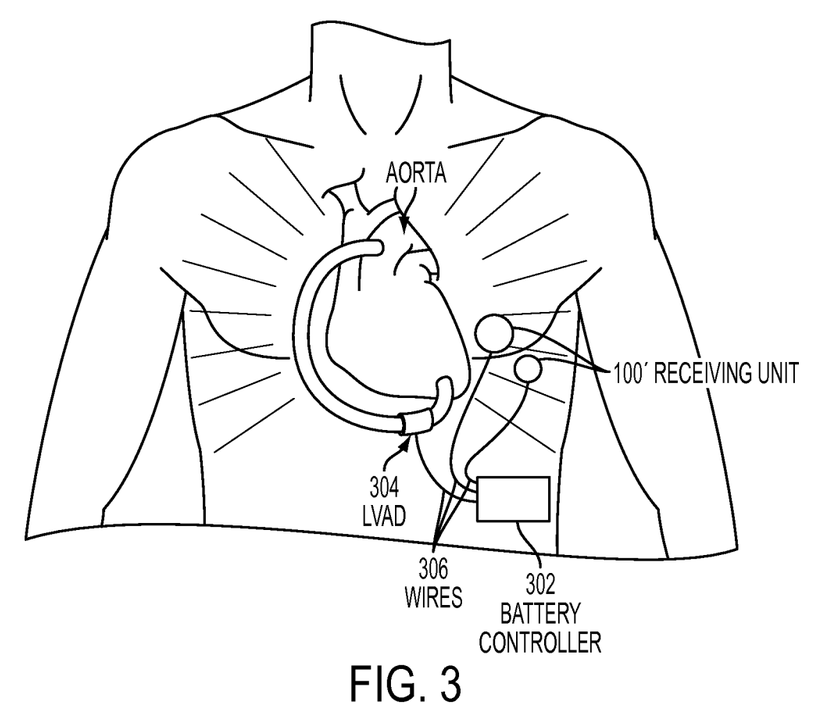
FIG. 3 shows a receiving unit (generator with a permanent magnetic coupling device attached to its shaft), battery/controller, and left ventricular assist device (LVAD). No redundancies in the system are shown. The sending unit is not shown, but it would overlie the receiving unit.

FIG. 3 shows a receiving unit (generator with permanent magnetic coupling device attached to its shaft), battery/controller 302 and left ventricular assist device (LVAD) 304 connected to the battery/controller 302 by wires 306. For redundancy, multiple receiving units 100' can be provided. The sending unit or units 100 are not shown; however, in use, they would overlie the receiving unit or units 100'.

Figure 4:
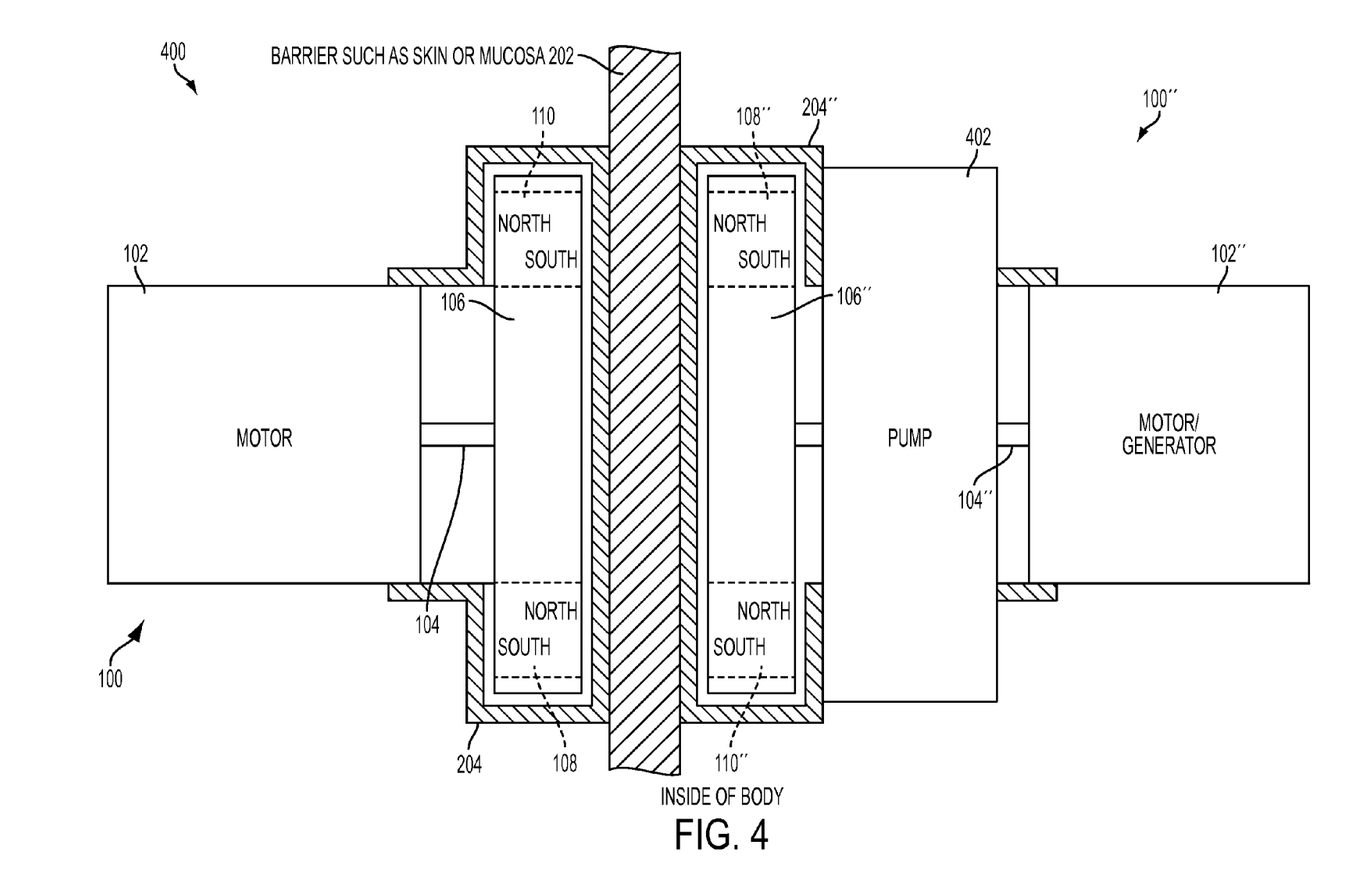
FIG. 4 shows a direct-drive pump with a motor/generator for charging the battery and driving the pump.

FIG. 4 shows a system 400 including a direct drive pump with a motor/generator for charging the battery and driving the pump. Outside of the body, the sending unit 100 and its components are the same as described previously. Inside of the body, a receiving unit 100" includes, in a housing 114", a motor/generator 102" connected by a shaft 104" to a rotor 106" having magnets 108", 110" and also to a pump 402. Such a receiving unit 100" can charge a battery and drive the pump simultaneously.

Figure 5:
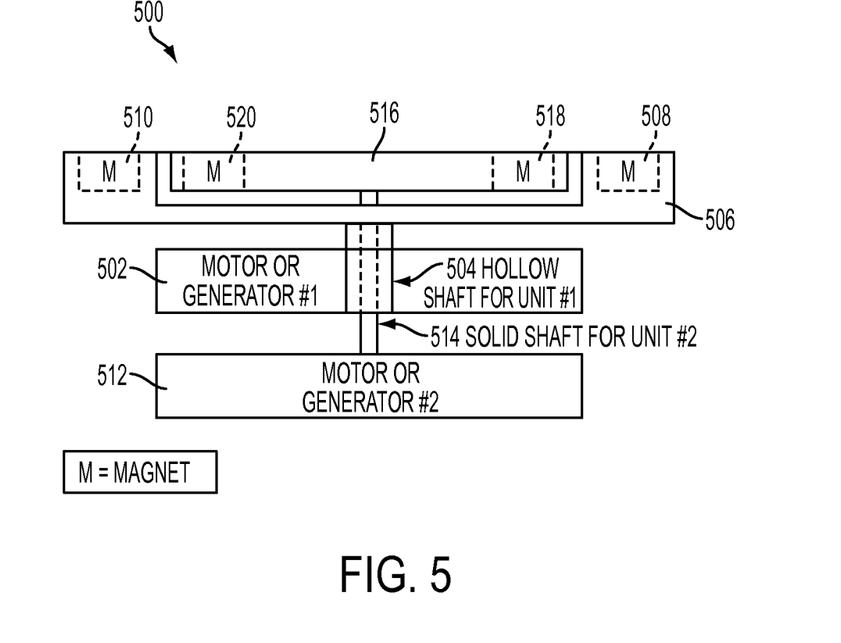
FIG. 5 shows a counter-rotating mechanism that could counteract torque in the sending and receiving units. The bars or disks holding the permanent magnets would spin in opposite directions to counteract each other's torque. Both bars or disks could be driven by one motor. Alternatively, each bar could have its own motor or could be driven by multiple motors. Both bars could drive one generator, or each bar could drive one or more generators.

FIG. 5 shows a counterrotating sending or receiving unit 500. The assembly 500 includes a first motor or generator 502 with a hollow shaft 504 for connection to an outer rotor 506 with magnets 508, 510 and a second motor or generator 512 with a solid shaft 514 for connection to an inner rotor 516 with magnets 518, 520.

Figure 6:
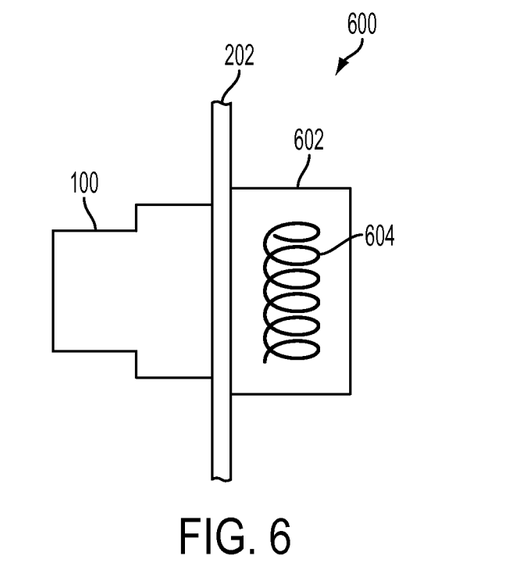
FIGS. 6 and 7 show configurations including permanent magnets and a coil.

FIG. 6 shows a system 600 in which the sending unit 100 described above is positioned outside of the body. Inside of the body, a receiving unit 602 includes a coil 604. The movement of the magnets in the sending unit 100 induces a current in the coil 604.

Figure 7:
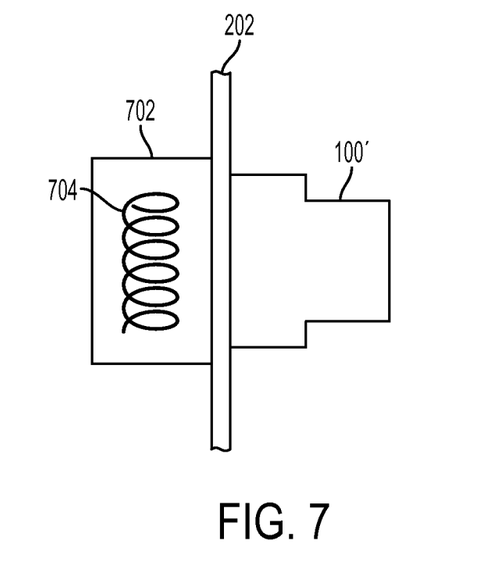

FIG. 7 shows a system 700 in which the receiving unit 100' described above is positioned inside of the body. Outside of the body, a sending unit 702 includes a coil 704. Current in the coil 702 causes a magnetic field which in turn causes movement of the magnets in the receiving unit 100'.

While preferred embodiments have been set forth above, those skilled in the art will realize that other embodiments can be realized within the scope of the invention. For example, the use of singular or plural terms in the present application should not be construed to exclude plural or singular elements, respectively. Moreover, disclosures of specific battery technologies and other technologies are illustrative rather than limiting; any other suitable technologies, now known or later developed, could be used instead. Therefore, the present invention should be construed as limited only by the appended claims.

I claim:

1. A system for transcutaneous magnetic energy transfer, the system comprising:
    a first component for implantation in a patient's body, the first component comprising a receiving unit comprising a rotor having permanent magnets circumferentially arranged around the rotor, a generator mechanically coupled to the rotor, and a housing for isolating the rotor, magnets and generator from the patient's body;
    a first connection for connecting the rotor of the first component to a medical device in the patient's body to power the medical device; and
    a second component for placement outside of the patient's body and for placement in close proximity to the first component while in use, the second component comprising a sending unit comprising a rotor having permanent magnets circumferentially arranged around the rotor, a motor mechanically coupled to the rotor, and a housing for retention of the rotor, magnets and generator.

2. The system of claim 1, wherein the rotor of the first component is rotated by the magnetic force exerted on it by the rotor of the second component while in use.

3. The system of claim 1, wherein in use rotational energy is transferred from the motor of the second component to the rotor of the second component and then by way of magnetic coupling to the rotor of the first component and then to the generator of the first component.

4. The system of claim 1, further comprising a battery to which the generator of the first component is connected.

5. The system of claim 4, wherein the battery is a lithium titanate battery.

6. The system of claim 1, wherein the first connection comprises a mechanical connection between the first component and the medical device.

7. The system of claim 6, wherein the medical device comprises a pump.

8. The system of claim 6, wherein the first connection comprises an electrical connection between the first component and the medical device.

9. The system of claim 1, wherein the first component further comprises an electromagnetic bearing or bearings for floating the rotor.

10. A system for transcutaneous magnetic energy transfer, the system comprising:
    a first component for implantation in a patient's body, the first component comprising a first movable object comprising a ferromagnetic material, a generator mechanically coupled to the first movable object such that mechanical movement of the first movable object is transferred to the generator and movement of the generator in turn generates power, a housing containing the first movable object, and a first connection for supplying power to a medical device; and
    a second component for placement outside of the patient's body, the second component comprising a second movable object comprising a permanent magnet, a motor mechanically coupled to the second movable object such that mechanical movement of the motor is transferred to the second movable object, a housing containing the second movable object and a second connection for receiving power from a source of energy.

11. The system of claim 10, wherein the permanent magnet is rotatable.

12. A ventricular assist device and power system comprising:
- a ventricular assist device for implantation in a patient's body;
- a first component for implantation in a patient's body, the first component comprising a first movable object comprising a ferromagnetic material, a generator mechanically coupled to the first movable object such that mechanical movement of the first movable object is transferred to the generator and movement of the generator in turn generates power, a housing containing the first movable object, and a first connection for supplying power to the ventricular assist device; and
- a second component for placement outside of the patient's body, the second component comprising a second movable object comprising a permanent magnet, a motor mechanically coupled to the second movable object such that mechanical movement of the motor is transferred to the second movable object, a housing containing the second movable object and a second connection for receiving power from a source of energy.

13. The ventricular assist device and power system of claim 12, wherein a plurality of at least one of the components is provided to provide redundancy in the ventricular assist device and power system.

14. The ventricular assist device and power system of claim 12, further comprising a controller which integrates control or telemetry functions for at least one of a pacemaker and a defibrillator.

* * * * *